United States Patent [19]

Miller

[11] Patent Number: 5,658,323
[45] Date of Patent: Aug. 19, 1997

[54] METHOD AND APPARATUS FOR DERMATOLOGY TREATMENT

[76] Inventor: Iain D. Miller, 26 Tremont St., Charlestown, Mass. 02129

[21] Appl. No.: 546,791

[22] Filed: Oct. 23, 1995

Related U.S. Application Data

[60] Provisional application No. 60/001,077 Jul. 12, 1995.

[51] Int. Cl.$^6$ .................................................. A61N 5/06
[52] U.S. Cl. .................................................. 607/89; 606/9
[58] Field of Search ........................... 607/89–91; 606/2, 606/3, 9, 10, 11

[56] References Cited

U.S. PATENT DOCUMENTS

| | | | |
|---|---|---|---|
| 3,538,919 | 11/1970 | Meyer . | |
| 3,693,623 | 9/1972 | Harte et al. . | |
| 3,834,391 | 9/1974 | Block . | |
| 4,388,924 | 6/1983 | Weissmann et al. . | |
| 4,564,011 | 1/1986 | Goldman . | |
| 4,617,926 | 10/1986 | Sutton . | |
| 4,733,660 | 3/1988 | Itzkan . | |
| 4,829,262 | 5/1989 | Furumoto | 330/4.3 |
| 4,836,203 | 6/1989 | Müller et al. . | |
| 4,854,320 | 8/1989 | Dew et al. . | |
| 4,917,084 | 4/1990 | Sinofsky . | |
| 5,059,192 | 10/1991 | Zalas | 606/9 |
| 5,217,455 | 6/1993 | Tan | 606/9 |
| 5,226,907 | 7/1993 | Tankovich | 606/9 |
| 5,258,989 | 11/1993 | Raven | 372/6 |
| 5,259,380 | 11/1993 | Mendes et al. . | |
| 5,282,797 | 2/1994 | Chess | 606/9 |
| 5,290,273 | 3/1994 | Tan | 606/9 |
| 5,304,170 | 4/1994 | Green | 606/9 |
| 5,330,517 | 7/1994 | Mordon et al. . | |
| 5,334,191 | 8/1994 | Poppas et al. . | |
| 5,344,418 | 9/1994 | Ghaffari | 606/9 |
| 5,405,368 | 4/1995 | Eckhouse . | |
| 5,425,728 | 6/1995 | Tankovich | 606/9 |
| 5,474,549 | 12/1995 | Ortiz et al. | 606/9 |
| 5,522,813 | 6/1996 | Trelles | 606/2 |
| 5,527,350 | 6/1996 | Grove et al. | 607/89 |
| 5,558,667 | 9/1996 | Yarborough et al. | 606/9 |

OTHER PUBLICATIONS

"Photosclerosis of cutaneous vascular malformations with a pulsed 810 nm diode laser" by Lawrence S. Bass of Columbia University College of Physicians & Surgeons, New York, NY *SPIE* 2395, 559–565 (Apr., 1995).

Press Release, Carried by Business Wire, dated Sep. 8, 1995, Authored by Palomar Medical Technologies, Inc.

Advertisement for Market Study entitled "Laser–Based Hair Removal" by Michael Moretti & Iain Miller of Medical Insight, Inc., Publication date: Feb. 1996.

Anderson et al., "The Optics of Human Skin," *The Journal of Investigative Dermatology*, vol. 77, No. 1, 13–19 (1981).

Anderson, RR "Selective Photothermolysis: precise microsurgery by selective absorption of pulsed radiation" *Science* 220, 524–527 (1983).

Balles et al., "Semiconductor Diode Laser Photocoagulation in Retinal Vascular Disease," *Ophthalmology*, vol. 97, No. 11, 1553–1561 (1990).

Duffy, "Small Vessel Sclerotherapy: An Overview," *Adv. Dermatol.*, vol. 3, 221–242 (1988).

Garden et al., "The Pulsed Dye Laser: Its Use at 577 nm Wavelength," *J. Dermatol. Surg. Oncol.*, vol. 13, No. 2, 134–138 (1987).

Goldman et al., "Continuing medical education (Dermatologic surgery)," *Journal of the American Academy of Dermatology*, vol. 17, No. 2, part 1, 167–184 (1987).

Goldman et al., "Pulsed–Dye Laser Treatment of Leg Telangiectasia: With and Without Simultaneous Sclerotherapy," *J. Dermatol. Surg. Oncol.*, vol. 16, No. 4, 338–344 (1990).

Miller, ID "Lasers in Plastic Surgery" PhD thesis, University of Strathclyde, Glasgow, Scotland, 1990 (abstract).

*Primary Examiner*—Angela D. Sykes
*Attorney, Agent, or Firm*—Lahive & Cockfield, LLP

[57] ABSTRACT

A laser treatment method is provided which removes vascular and pigmented lesions from the skin of a living human. The methodology involves a carefully designed treatment protocol utilizing a modified optical apparatus. The apparatus is a modified diode laser system, designed for optimal therapeutic selectivity.

11 Claims, 4 Drawing Sheets

METHOD AND APPARATUS FOR DERMATOLOGY TREATMENT

CLAIM TO BENEFIT OF EARLIER FILING DATE

This application claims the benefit of the prior filed co-pending provisional application Ser. No. 60/001,077, filed on Jul. 12, 1995 for "METHOD AND APPARATUS FOR PARAMETERS FOR LASER MEDICAL PROCEDURE", pending.

FIELD OF THE INVENTION

The present invention is directed to the removal of vascular and other pigmented lesions from the skin utilizing a modified high power diode laser system under carefully controlled conditions.

BACKGROUND

Human skin may contain a range of abnormalities including vascular and pigmented lesions. Although not always dangerous to the individual, such abnormalities are frequently cosmetically troublesome.

Vascular lesions, in particular, may take several manifestations. Common examples are 'port wine' stain birthmarks; telangiectasias (spots or vessel lines formed by dilated capillaries or other small blood vessels); and hemangiomas (benign tumors composed of well-formed blood vessels).

Leg telangiectasia, or 'leg veins', are chronically dilated blood vessels visually apparent as red or blue linear or 'spider' structures. They may cover extensive or local areas of the leg and are more common in women. Large diameter vessels may cause discomfort, while smaller diameter vessels are more often considered cosmetically unsightly by patients.

Up to 80 million adults in the United States alone are affected by leg veins. It is estimated that 29–41% of women and 6–15% of men worldwide have 'abnormal' (visually apparent) leg veins. Most vessels presenting for treatment are less than 1 mm in diameter.

The vessels consist of dilated blood channels in an otherwise normal dermal stroma. The blood channels have a single endothelial cell lining with thickened walls consisting of collagen and muscle fibers. Clinically, these vessels may be categorized as linear, arborizing, spider or papular.

Such dilated vessels may result from pregnancy or the use of progestational agents. A genetic link is usually also present. Some such veins are associated with a high pressure flow from a feeding reticular or varicose vein.

In order to eradicate a leg vein, it is usual to damage the endothelial vessel lining or surgically ligate the vessels. Such surgery is radical and performed on an in-patient basis. Endothelial damage may be induced by means of Sclerotherapy or by the use of light energy on an outpatient basis.

Sclerotherapy is currently the favored method of non-surgical leg vein eradication.

Sclerosing agents have traditionally been employed to damage endothelial cells. Such agents as sodium tetradecyl sulfate, hypertonic saline and polidocanol are injected into large vessels (>1 mm in diameter) and result in death of the endothelium. Several systemic injections to a 'feeder' vessel system may result in widespread death of the ectatic vessels.

The use of sclerosing agents is associated with telangiectatic matting (formation of clusters of small vessels) in 35% of patients treated, and with hyperpigmentation (residual brown pigmentary staining) in up to 30% of vessels treated. Other adverse sequelae are possible, including ulceration, edema (blistering) and systemic anaphylactic shock. Vessel recurrence within 5 years has been observed in up to 40% of patients studied. Further, many patients are fearful and resistant to the use of needles.

Hyperpigmentation pursuant to sclerotherapy is particularly troublesome, as it replaces the blue vessels with a brown discoloration which may persist for up to 5 years. This effect results from the catabolism of extravasated blood to hemosiderin, a form of iron deposition, brown in color, which may reside in the proximal dermis for up to 6 months.

Sclerotherapy injection difficulties render sclerotherapy relatively unsuitable for the routine treatment of vessels with diameters of less than 1.0 mm.

Light energy has been utilized for the treatment of cutaneous vasculature.

When use of light is under consideration, one can choose to vary wavelength, pulsewidth or coherence (uniformity). Wavelength will typically be chosen by consideration of the absorption and scattering characteristics of the target tissue layers. The absorption characteristics are typified by several peaks in the visible region of the spectrum, due to target chromophores, together with a monotonic decrease into the infra-red region. The scattering of tissue decreases monotonically through the visible to the near infra-red region and beyond.

Both coherent laser light and incoherent light from a flashlamp-type source offer the potential for high selectivity of treatment. Short wavelength (<500 nm) light is usually not employed, since it is highly scattered in tissue and therefore unable to penetrate to a sufficient depth. Light of a wavelength greater than 500 nm has been employed for the treatment of vascular lesions. The absorption profile of whole blood is shown in FIG. 1. This profile will vary with anatomical location, since blood constitution varies, but can be taken as generally representative.

Vascular diseases characterised by small vessels such as the Port Wine Stain respond well to visible wavelength pulsed laser light from a pulsed dye laser, typically with a wavelength in the 550–600 nm range, which is tuned to a local absorption peak of the intravascular blood. Such light, which is absorbed in the top 0.05 mm of the vessel, can coagulate and thereby thrombose a significant portion of the entire cross section of small vessels (<0.1 mm). Construction of such a pulsed dye laser for dermatology applications has been described previously.

Visible wavelength laser light is less effective on larger diameter vessels (>0.1 mm). Although vessel rupture is possible, this represents a non-optimal mechanism associated with the involvement of only the superficial portion of the vessel, due to the shallow absorption depth of the light. Regrowth of the insufficiently damaged vessels usually occurs under these circumstances. Also, the rupture of the vessel leads to an unsightly post-treatment purpura ('bruising) which can persist for up to 2 weeks. This is not well tolerated by patients. It should be remembered also that dilated vasculature of the extremities is also associated with a different ratio of oxy/deoxygenated hemoglobin, the main absorbing chromophores within the blood. A typical leg vein is filled predominantly with deoxygenated hemoglobin, responsible for its blue color. Oxygenated hemoglobin, as typically found in port wine stains on the face, is bright red in color. The near infra-red absorption characteristics of the two principal blood types is shown in FIG. 2. Both hemoglobin types have equal absorption around 800 nm, rendering absorption independent of chromophore mix (and hence of anatomical location) at this wavelength. The magnitude of the absorption coefficient around 810 nm is well suited to the dimensions of the target vessels.

A further disadvantage associated with existing short wavelengh coherent laser sources such as the pulsed dye laser is their short pulsewidth. With a maximum around 1.5 milliseconds, no time for concurrent conduction of the heat is permitted. A pulsewidth of several tens of milliseconds would be desirable. Also, the high cost and the significant bulk of the componentry associated with such devices are prohibitive factors.

A broadband-emitting incoherent flashlamp light source may offer an alternative approach for the treatment of leg veins. Such a source may utilize a spread of principally infra-red wavelengths (550–1200 nm) most of which exhibit a smaller degree of absorption better suited to larger vessels. A longer pulsewidth of up to 100 milliseconds is also available, permitting concurrent heat conduction through the vessel. As a consequence, the full volume of the vessels may be affected, as required for vascular necrosis.

Clinical results from the use of this class of source are at the preliminary stage and may include an obviation of the hyperpigmentation associated with the shorter wavelength/pulsewidth dye laser since proximal rupture is no longer the mechanism in effect. Adverse effects include the occurrence of gross heating effects, edema and blistering associated with the incoherent light, since incoherent light has poor penetration characteristics in human tissue.

Further, the system is physically clumsy and difficult to use. Also, this incoherent light cannot be easily focused to a spotsize which efficiently overlaps the vessels and hence unaffected tissue is involved in the pathological effects. These disadvantages, taken together, limit the applicability of this technology.

Another manifestation of the incoherent flashlamp based light source relates to the use of a mercury-xenon vapor lamp, with specific emission peaks in the visible portion of the spectrum. This incoherent source will result in gross heating of proximal tissue, with a resultant need for concurrent cooling of the skin. Further, the visible emission spectrum of the lamp lends its use to small vessels found in Port Wine Stains, since the light will be absorbed in the top 0.05 mm of the vessels. Larger leg veins are not cited in this patent for this reason.

FIG. 3 illustrates graphically the effect of tuned visible (~580 nm) and near infra-red (700–900 nm) coherent light on small (<0.1 mm) and moderate (0.1 mm<diameter<1.0 mm) sized vessels. This figure illustrates the inherent suitability of visible band light to small vessels and of infra-red band light to moderately sized vessels, since destruction of a significant proportion of the vessel is required. This suitability is harnessed only if pulsewidths of the order of several tens of milliseconds are available, with their concurrent conduction permitting useful proximal vessel wall damage. In this figure, the shading shows the heat generation during the pulse. The denser shading associated with visible light signifies the attainment of high temperatures with associated explosive effects. This heat can be expected to conduct further to affect a peri-vascular tissue volume.

A near infra-red narrow-band coherent laser light source with variable pulsewidth would offer the potential for more thorough coagulation of larger vessels, without the adverse effects attendant with the flashlamp source. Further, such a source would penetrate to the required depth in tissue. An alternative source of near infra-red light and associated treatment method is described in the following sections.

SUMMARY OF THE INVENTION

The present invention comprises a laser treatment method and apparatus for the removal of vascular and other pigmented lesions from the skin.

The treatment method, according to one embodiment of the invention, includes:

Irradiation of the skin with power level in the range 10–60 Watts, pulsewidth 1–99 milliseconds, and spotsize 1 mm with coherent pulsed light with wavelength in the range 700–1000 nm, controlling the applied radiation such that desired endpoints are observed during treatment, consisting of mild 'blanching' without significant pigmentary or textural change, allowing the skin to heal for a period of 2–16 weeks, irradiating on 0–5 subsequent occasions with additional exposures, One apparatus for practising the foregoing embodiment consists of:

a modified high power semiconductor diode laser system with pulsewidth variable from 1–99 milliseconds.

The invention incorporates a modified laser apparatus with new application, together with a novel treatment method for the eradication of leg veins. The new treatment thus developed presents the potential for numerous significant advantages, particularly relating to minimization of hyperpigmentation while optimally targeting a cosmetically significant range of leg vessels. This development of a clinically effective therapeutic treatment using a carefully controlled modified laser apparatus with associated minimization of adverse effects is a major improvement and advance over current options.

BRIEF DESCRIPTION OF THE DRAWINGS

For a fuller understanding of the nature and objects of the invention, reference may be had to the following detailed description and the accompanying drawing, in which.

DETAILED DESCRIPTION OF THE INVENTION

Theoretical Considerations

As discussed in the foregoing, it is first necessary to identify an optimal wavelength and pulsewidth regime.

Figure 1:
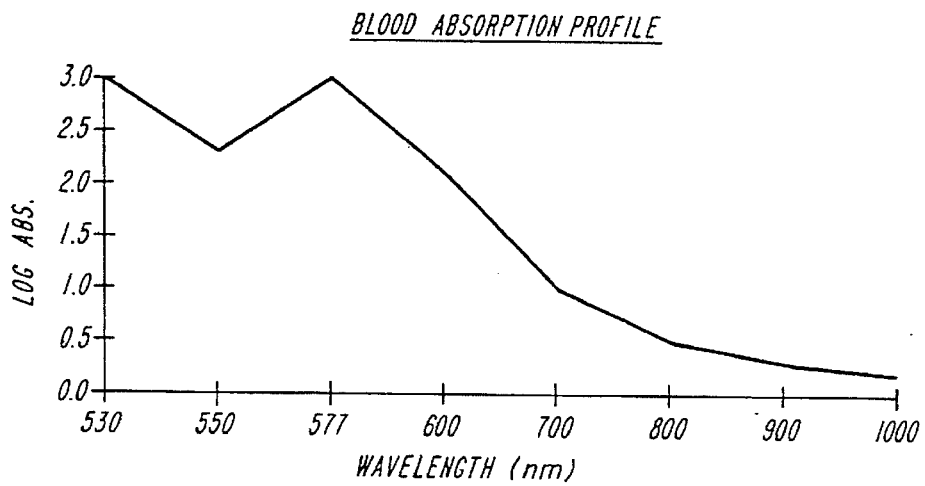
FIG. 1 is a graph showing a typical absorption profile of whole blood.
Figure 2:
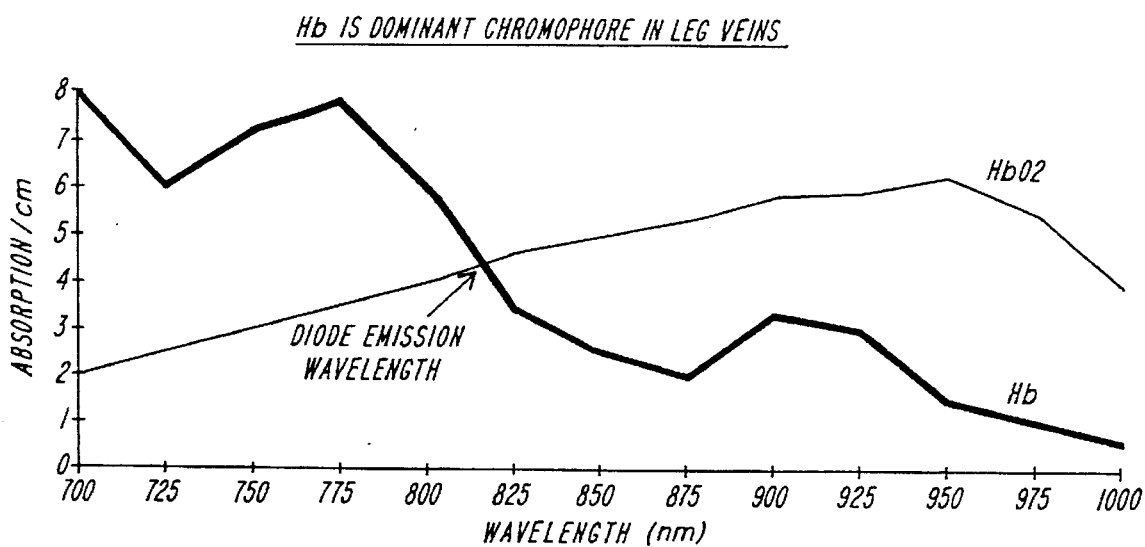
FIG. 2 is a graph illustrating the near infra-red absorption characteristics of two principal blood types.
Figure 3:
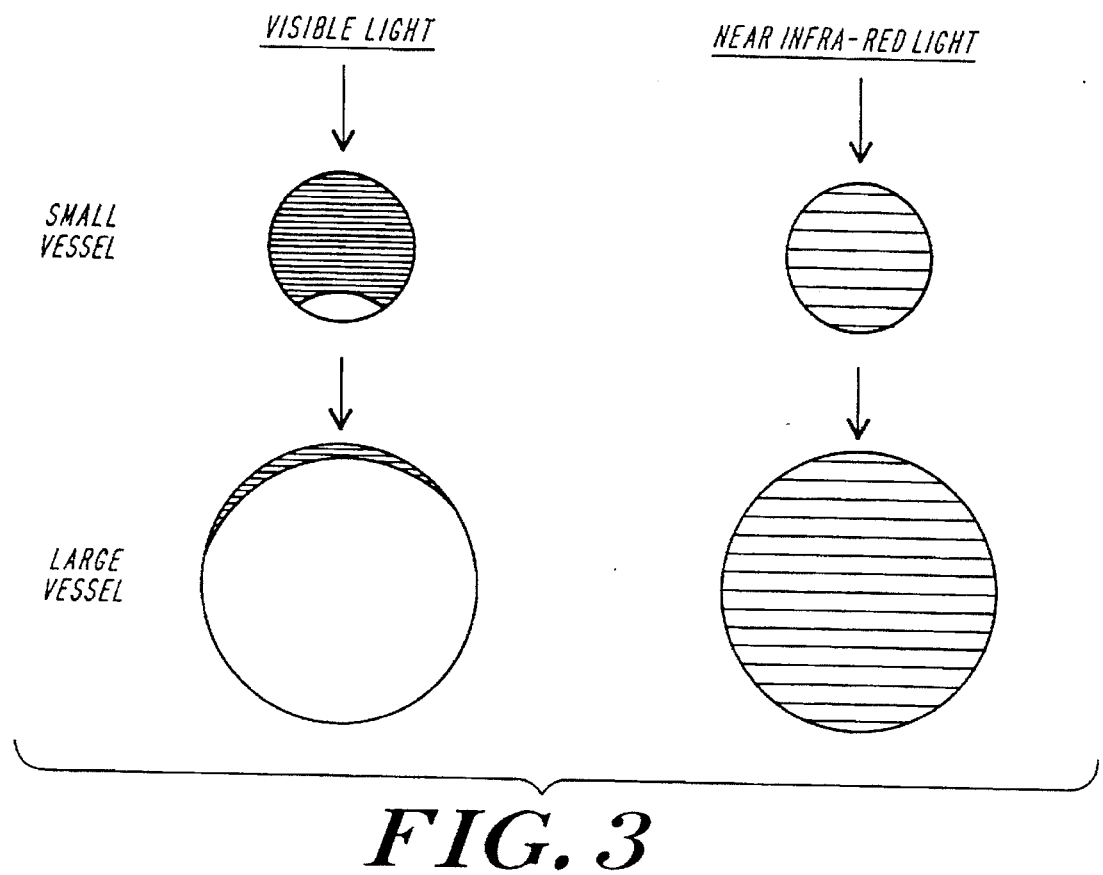
FIG. 3 is a graph illustrating the effects of tuned visible light and of near infra-red coherent light on small and on moderate sized blood vessels.

In terms of wavelength, a lower absorption coefficient than those exhibited in the visible spectral region is desirable to affect the entire volume of larger vessels. To fill a 1 mm diameter vessel, for example, an absorption coefficient in the range 1–10 cm$^{-1}$ would be optimal, as compared with the absorption coefficient at the yellow wavelength of 585 nm of 300 cm$^{-1}$. As shown in FIG. 2, the near infra-red wavelength range (700–1000 nm) presents absorption coefficients in this range. This graph illustrates the absorption characteristic of oxy and deoxygenated hemoglobin, the dominant blood chromophores.

Figure 4:
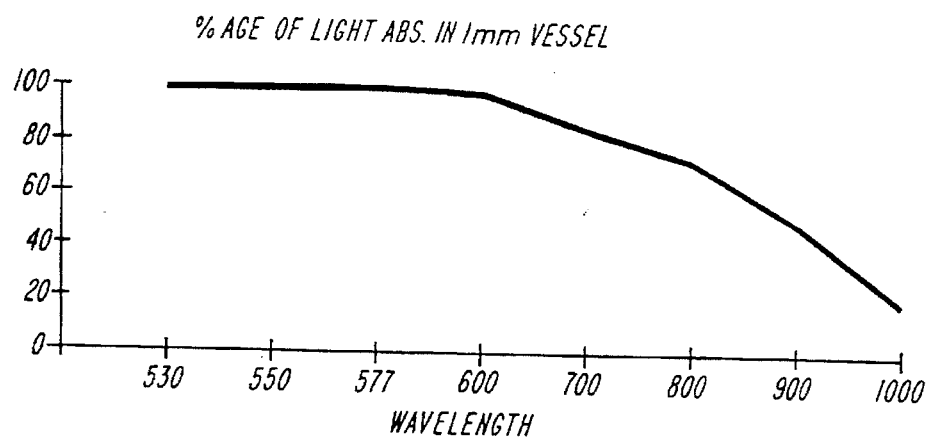
FIG. 4 is a graph indicating percentage of light absorption in a one millimeter diameter blood vessel as a function of illuminating wave length.

Although the absorption coefficient is significantly less in the near infra-red than that found in the yellow visible region, the thickness of leg vessels is such that the incident energy is effectively utilized throughout the depth of the vessel. Hence, an equivalent proportion of the applied total energy may be absorbed in the vessel in each case, with greater uniformity of deposition for the near infra-red region. This effect, shown in FIG. 4, indicates that the specificity of action is only ultimately lost for wavelengths above 1000 nm, where a significant portion of the light passes through the vessel. In the 530–900 nm spectral region, most of the light is utilized in a 1 mm vessel. For larger vessels in the range 1–2 mm, almost all of such light will be utilized. The precise selection of wavelength determines the uniformity of absorption of the light.

Figure 5:
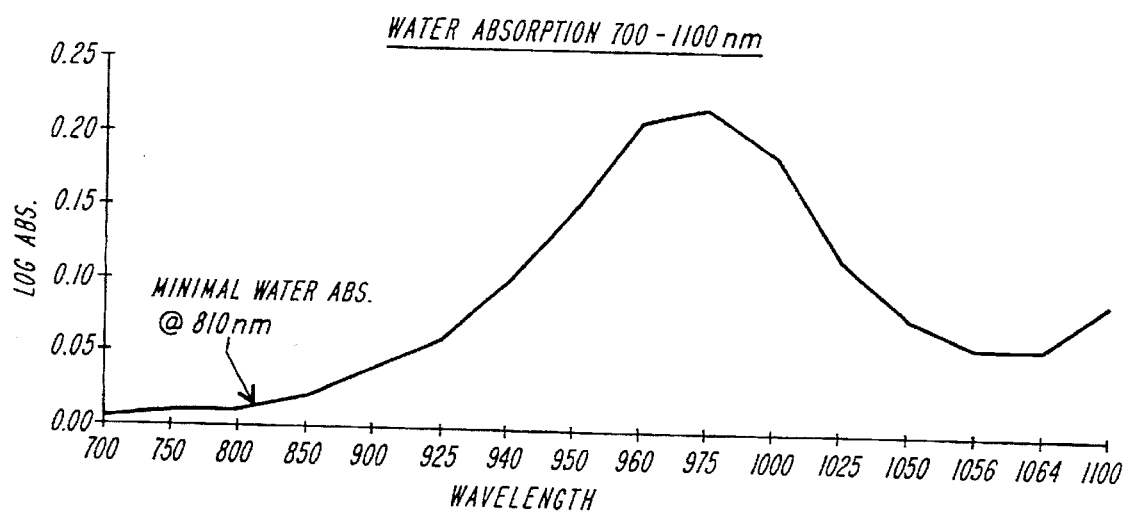
FIG. 5 is a graph illustrating water absorption in a blood vessel as a function of illuminating wave length.

It is also important that tissue water absorption be minimized in order that maximum depth of penetration be attained. Water absorption, shown in FIG. 5, presents a peak at 980 nm and other peaks further into the infra-red. To avoid this broad peak and operate at a reliable wavelength for the laser, a laser source emitting in the 800–850 nm range may be considered optimal. Water absorption at 810 nm, for example, may be considered negligible.

Selection of pulsewidth is of equal importance. It is critical that the resultant heat production is unable to conduct widely into the surrounding dermis, but that a partial conduction is desirable. This dictates that the applied pulse duration of the energy be well matched to the mechanical characteristics of the absorbing vessels. For a vessels with size in the range 0.1–1.0 mm, a favorable pulsewidth regime is likely to be in the range 1–100 milliseconds, corresponding to a match with the 'thermal relaxation time constant' of the target.

To further validate this thought process, a computer technique known as Monte-Carlo modeling may be undertaken to simulate the effect of such laser light. This intensive approach generates many millions of optical events in the skin to ultimately derive optical energy distributions. In this modeling, a sample 0.5 mm thick blood layer was assumed at a 0.5 mm depth beneath a highly scattering epidermal/dermal top layer. This model yields an optical distribution which may be converted to a thermal distribution by means of the calculations below.

$$\Delta T = E / C \times M$$

where

ΔT=temperature rise in small tissue segment

E=energy deposited in tissue segment=no. of photons× photon energy

C=specific heat capacity of tissue

M=mass of tissue segment.

Tissue parameters, such as scattering and absorption, as used in this model were obtained from the literature, although it should be noted that no previous modeling work is evident which addresses the clinical problem of leg veins.

Figure 6:
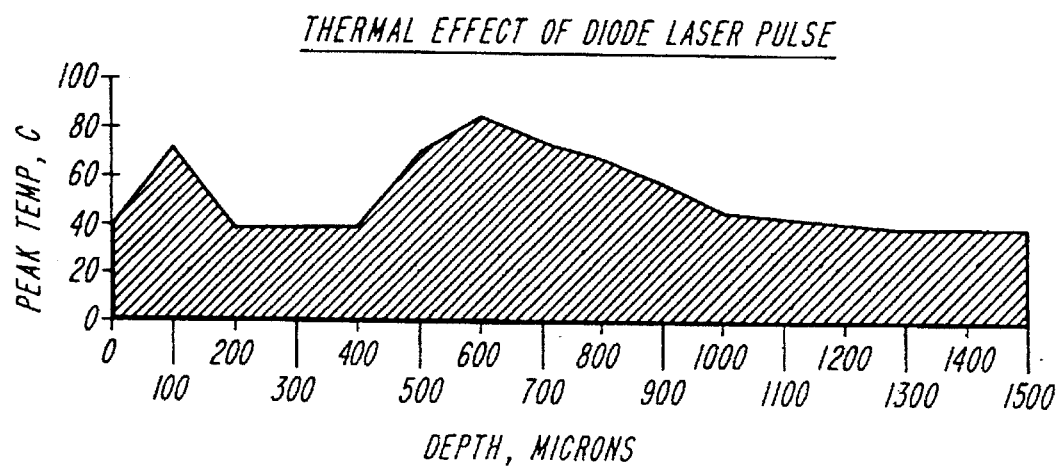
FIG. 6 is a graph illustrating the thermal effect of a diode laser pulse as a function of tissue depth.

Various power and energy levels were used in the modeling. As an example, FIG. 6 illustrates the thermal profile at the end of an exposure of 20 Watts of 800 nm laser light at this wavelength. Various beam spotsizes and pulsewidths were modeled. In FIG. 6, a spotsize of 1 mm, combined with a pulsewidth of 30 milliseconds, were employed (note that the blood vessel surface begins at a depth of 500 um). The temperatures shown are sustained in the blood vessel beyond the duration of the exposure (30 milliseconds), providing sufficient locally deposited energy to kill the vessel. The thin epidermal layer loses heat more rapidly and is thereby spared from gross epidermal damage. Minimal perivascular heating is expected for appropriate pulse durations (10–100 milliseconds).

This graph illustrates that, while light in the 800–850 nm region has relatively low absorption, a preferential effect on the vasculature may still be induced.

From the above theoretical studies, it has become apparent that a laser source emitting in the wavelength region 800–850 nm, with variable pulsewidth and spotsize capabilities, will meet the conditions required for optimal clinical treatment of leg vessels with diameters in the range 0.1–1.0 mm. Larger vessels may also respond. It is important that the source be a laser, with its attendant coherence, rather than an incoherent source such as, for instance, a flashlamp-based source. Coherent light is unidirectional in nature and better suited to penetration through turbulent human tissue.

In the modeling example cited above, as stated, a vessel of diameter 0.5 mm at depth 0.5 mm was brought to damage threshold by means of a 20 Watt source with 1.0 mm spotsize, operating with a pulsewidth of 30 milliseconds. To allow for deeper, thicker vessels, and for modeling limitations, I have calculated that a source with up to 60 Watt capability and pulsewidth variability in the range 1–99 milliseconds would provide greater clinical flexibility.

Further, adverse sequelae associated with currently available technologies will be reduced. In particular, purpura and post-treatment hyperpigmentation associated with mechanical rupture and extra-vasation will be greatly reduced, as the longer pulsewidths produce a more uniform effect. Also, deeper penetration of the long 800 nm wavelength will improve treatment efficacy.

The above represents a summary of the theoretical considerations employed to calculate an appropriate parameter set. As part of this invention, an appropriate apparatus and treatment method were also devised.

Apparatus

It was determined after a review of the scientific literature, that some manifestation of diode laser technology would be capable of providing the requisite parameter set.

Semiconductor diode laser technology, first developed in 1962, today finds application in devices ranging from consumer electronics and communications to medicine.

A basic system, in the high power configuration envisaged here, consists of an electronic power supply coupled to a semiconductor crystal encapsulated in an optical chamber capable of capturing and harnessing optical emissions from the crystal. When a large direct current is passed through the crystal, optical emission is generated and amplified. A beam of light results, with a high degree of brightness and directionality.

The basic system is further refined by means of the addition of thermo-electric cooling circuitry for temperature stabilization and of electronic circuitry for exposure control and pulsewidth generation. Maintenance needs are minimal, with a 5000+ hour life on the sources equating to several years of use.

Individual diode elements have limited output power capability and beam shapes which are not amenable to ease of delivery to distant sites. Recent efforts have concentrated on beam shaping and combination of beams from a plurality of single elements. Each single element can deliver up to 1 Watt of CW power.

As a consequence, by means of the combination of beams from many such elements on diode bars, it is now possible to deliver tens of watts of diode laser light through flexible fiber optical cable to a distant site. These high power levels as recently demonstrated by other inventors (up to 100 Watts) have made possible the new treatment concept outlined previously, in which such a source, appropriately modified, may be used for the current application.

A number of medical device companies have packaged diode laser systems for medical use, based on the above OEM subcomponents. Use of their finished systems is advocated for urology, gynecology, general and plastic surgery, gastroenterology and ENT. None of these applications are directly vascular in nature. Some ophthalmic applications have also been studied in which small retinal vessels were treated with a lower power (up to 1.3 Watts) diode laser. It has been shown that small vessels (<200 um) could be coagulated, but that optimal use would entail the use of an adjunctive sensitizer dye such as indocyanine green. Larger vessels were not studied. No direct vascular use of the diode laser in Dermatology has been studied at this time.

Diode laser systems as described above have been utilized for general surgical applications on soft tissue, whereby a non-specific cutting action results from the delivery of long pulses of light (>100 milliseconds pulsewidths are available from the devices), with power levels in the range 1–60 Watts. In this mode, such a device acts as an optical scalpel, with some associated coagulative potential. Shorter pulsewidths are currently not commercially available from medical manufacturers of this technology.

One embodiment of the invention involves the modification of such a system by means of electronic control circuitry to obtain shorter pulsewidth (1–99 millisecond) operation.

The practice of the invention harnesses the specific targeting potential of the device by means of a careful control and administration of the parameters as modeled previously. By this means, light is to pass through overlying tissue, affecting only the desired target vessels. Direct targeting of large blood vessels on the legs with a high power (~10–60 Watts) and short pulsewidth diode source has never previously been studied or attempted.

The invention consists of a clinical treatment methodology for the eradication of unwanted leg vessels, described in the next section. The treatment method employs modified specific optical apparatus which is described in this section in terms of preferred and alternative embodiments. The combination of parameters described below under 'preferred specification' have not so far been utilized in Dermatology and may not have been used in any other medical specialty. One preferred specification for the device is listed below:

| Host material | GaAs semiconductor laser source |
| --- | --- |
| wavelength range | 800–850 nm |
| pulsewidth | 5–99 milliseconds |
| power level | 10–60 Watt, 1 Watt increments |
| repetition rate | 1–20 Hz. |
| spot size on skin | 0.5–1.5 mm, variable |
| delivery system | fiber, with dermatology handpiece termination |

-continued

| laser cooling method | thermoelectric |
| --- | --- |
| pulsing method | electrical |
| aiming beam | red diode or helium neon laser (1–10 mW) |

This preferred embodiment can specifically be utilized for the treatment of leg vessels and may also find application in the treatment of facial telangiectasia, pigment removal and other Dermatological conditions.

A second alternative embodiment employs the use of a contrasting dye such as Indocyanine Green, which enhances absorption in the preferred wavelength region. This would be injected into the patient prior to treatment with the diode laser, in order to enhance the selectivity of the laser action.

A third alternative embodiment utilizes a different semiconductor material variant producing a wavelength in the range 850–1000 nm, with a power level in the range 1–60 Watts.

A fourth alternative embodiment utilizes a second host material 'pumped' by the diode laser. This host material, which itself would then lase at a different wavelength, might consist of a polymer encapsulated dye material, or some other glass or crystal structure doped with lasing ions.

Figure 7:
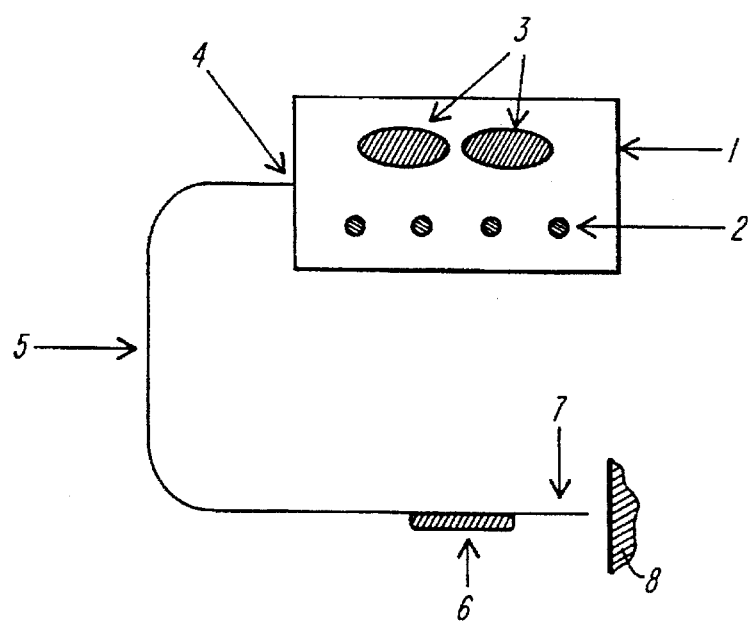
FIG. 7 is a block schematic representation of tissue treatment apparatus according to one practice of the invention.

All of the envisaged embodiments produce near infra-red light with pulsewidths and power levels amenable to the treatment of the targeted leg vessels as calculated previously. This first preferred embodiment is shown in FIG. 7::

In practice, a separate footswitch (not shown) provides triggering to the laser source found within the laser head cabinetry (1). The source consists of a set of arrays of individual laser diodes. Light from these diodes is typically collected in a series of individual small diameter fibers constituting a bundle. This bundle is grouped together physically within the cabinetry enclosure and light coupled via a high efficiency connector into a single larger diameter fiber. An external connector (4) provides an interface to an external length of optical fiber or light guide (5). This optical delivery media is then coupled into a handpiece (6) containing focusing lenses. These lenses, together with a distance gauge (7), provide precise positioning and focusing onto the patient's skin (8). Power level, repetition rate, and pulsewidth of the source are controlled by means of the electronic controls (2) which together provide access to the specification set listed previously. Displays (3) permit verification of the selected parameter set. An incorporated visible 'aiming beam', within the cabinetry enclosure, also delivered through the light guide, provides verification of the ultimate placement of the invisible treatment laser spot.

Clinical Treatment Methodology

The goal of the treatment is to lighten and eventually clear the vessel while leaving the surrounding normal skin intact and unaffected. Below is presented an optimal and novel therapeutic treatment methodology suitable for use in a variety of different clinical applications.

Dermatological applications and uses:
(i) Telangiectasia of the legs
(ii) Mature vascular lesions of the head and neck, including Portwine stains and telangiectasia
(ii) Epidermal and dermal pigment removal A number of major advantages and conveniencies are provided by the present treatment method including:

1. The present methodology envisages the use of a specific parameter set chosen to provide optimum selectivity of damage to the target tissue only. The epidermis and perivascular dermis are spared while damage is administered, in a controlled fashion, uniformly throughout the targeted vessels.

2. The vessels are uniformly coagulated rather than mechanically ruptured. This means that blood does not leak out of the vessels into the surrounding tissue. This leakage is responsible for the gross, and persistent, purpura and hyperpigmentation which is cosmetically troublesome to the patient. The present invention should minimize these risks.

3. The invention provides for the use of narrow-band coherent infra-red light. Such light is able to penetrate deep into the dermis with minimal scattering or competitive absorption and affect most of the visible vasculature.

4. The equipment used to provide the therapy can be manufactured at relatively low cost and has great ease of portability. This will ultimately result in greater patient access to the therapy.

5. The procedure is relatively gentle and painless, and obviates the use of multiple needle injections as associated, for instance, with sclerotherapy.

6. Several treatments are required. Each treatment will provide an occasion for the physician to tailor the parameters to the individual needs of the patient. Hence, the personal health, safety and cosmetic appearance of the skin are affected only to the extent required, and any side effects minimized.

7. Minimal damage is caused to surrounding skin structures, which do not absorb well at the near-infrared wavelengths. Water absorption is low, minimizing peri-vascular direct heating, and melanin absorption is low, minimizing epidermal pigmentary change and epidermal disruption. This is turn minimizes any complications associated with wound formation.

General treatment procedures and preferred details:

Vessels with size in the range 0.1–1.0 mm will respond best to treatment, however larger vessels may also be treated. Vessels with a powerful deep feeder vein are least likely to respond to treatment by any available method.

A power level in the range 10–60 Watts is used, with 30 Watts being a 'typical' value. An associated spotsize of 1 mm is used to efficiently overlap the vessel and make good use of the power capability of the laser system. A Pulsewidth in the range 1–99 milliseconds will be used, with the shorter end of this range being used for small vessels (~0.1 mm) and the longest pulsewidth being used for larger vessels (~1.0 mm). A wavelength in the range 800–850 nm is preferred.

After treatment, the site may be somewhat blanched (whitened) due to some coagulation of tissue. Some fine purpura may also be present, as a result of the intra-vascular coagulated blood.

An assessment will be made at the second visit relating to any color or texture change of the skin. The vessel itself will also be graded for any lightening. Absence of any lightening or adverse effects will be taken as indicative of the need to increase energy or exposure time. Occurrence of significant adverse sequellae will be taken as indicative of the need to decrease power and exposure parameters.

Detailed Protocol

The vessel group to be treated is photographed under controlled conditions and its diameter measured using a slide scale or needle. It is further examined to detect the prescence of scarring or otherwise abnormal color or texture.

Individual vessels are designated as test sites to which different carefully chosen parameters of laser light are applied. An initial set of parameters for smaller vessels (~0.1 mm) would be: 10 Watts of light, 1 mm spotsize, 10 millisecond exposure time. Larger vessels should be exposed at a more energetic parameter set. Several such spots would be placed linearly along one of the vessels comprising the test site. Different vessels within the group are exposed with increasing power levels or pulse durations. Increases will be in steps of 5 Watts and 10 milliseconds. Hence, parameter combinations of 10 Watt/10 ms; 15 Watt/ 20 ms; 20 Watt/30 ms; 25 Watt/40 ms; 30 Watt/50 ms will represent favorable increments, although other combinations are possible. Feedback is obtained from each application in terms of immediate tissue response and used to determine subsequent test site parameters.

Desired response includes a whitening of the vessel without abnormal texture or damage to the overlying tissue. Some reddening of the treated area is also desirable, which is associated with the inflammatory (erythemic) response of the body.

Following treatment, a topical antibiotic ointment may be applied to the treated site and the skin area covered with a dressing.

The patient will return after a specified healing period (usually 2–16 weeks) for evaluation and further treatment. These additional treatments (typically up to 5) will be administered with the parameters found to induce optimal vessel lightening with minimal adverse sequellae. Parameters will be adjusted if the response is inadequate (insufficient lightening) or too severe (induration, ulceration or pigmentary change to the overlying epidermis). In the former case, applied power and/or pulsewidth will be increased, while in the latter a decrease will be effected.

If a vessel does not respond after a total of 6 treatments, treatment should be discontinued. This is likely to be indicative of the presence of a high pressure underlying feeder vein system, or some other combination of adverse mechanical or biological characteristics. In any event, the patient should be followed for up to one year to note any incidence of recurrence.

I claim:

1. A laser treatment method for the removal of unwanted leg veins and other vascular and pigmented lesions from the skin of a human, said method comprising the steps of irradiating on a first occasion a chosen treatment site with pulsed coherent light with wavelength in the range 700–1000 nm, said irradiating light having an exposure spot size from 0.5 to 1.0 mm at the treatment site and having a power level of 20–60 Watts and a pulse duration of 30–99 milliseconds, said pulse duration being selected for partial conduction in the surrounding dermis, said treatment site containing vessels with diameter in the range 0.1–1.0 mm.

allowing the skin to heal typically for a time period of 2–16 weeks, and irradiating on 0–5 subsequent occasions each vessel so previously treated with pulsed coherent light with a wavelength in the range 700–1000 nm, said light having a power level of 20–60 Watts and a pulse duration of 30–99 milliseconds.

2. The laser treatment method recited in claim 1 wherein the pulsed coherent light has a wavelength in the region of 800–850 nm.

3. The laser treatment method recited in claim 1 wherein said irradiation on first occasion employs a greater total energy application than on subsequent occasions.

4. The laser treatment method recited in claim 1 wherein said irradiation on first occasion employs a lesser total energy application than on subsequent occasions.

5. The laser treatment method recited in claim 1 comprising the further step of injecting a sensitizing dye into a local venous system of a patient prior to each said irradiating step.

6. The laser treatment method of claim 5, wherein the sensitizing dye is indocyanine green.

7. A therapeutic treatment device for removal of unwanted leg veins and other vascular and pigmented lesions from the skin of a human, said device comprising a laser head containing power source, laser source, controls, and cooling electronics, an optical fiber connector and light guide optically coupled to the laser head for receiving light produced by the laser head, a dermatology handpiece and distance gauge for distance control of tissue contact, connected to the optical fiber, and control circuitry electronically connected to said laser head and controlling the generation of pulsewidths in the range 1–99 milliseconds, for effecting said removal of lesions.

8. The therapeutic treatment device of claim 7 wherein the laser is a semiconductor laser operating with wavelength in the range 800–850 nm.

9. The therapeutic treatment device of claim 7 wherein the laser is a semiconductor laser with modified control circuitry allowing for pulsewidth controllability in the range 1–99 milliseconds.

10. (New) The therapeutic treatment device of claim 7 wherein the laser source is adapted for total power emission in the range 10–60 Watts; pulsewidth variability in the range 1–99 milliseconds and wavelength variability in the range 700–1000 nm.

11. The therapeutic treatment device of claim 7 wherein the laser source consists of a diode laser pumped material such as dye-impregnated polymer or active ion doped glass or crystal host.

* * * * *